United States Patent [19]

Fujiwara et al.

[11] Patent Number: 5,238,811
[45] Date of Patent: Aug. 24, 1993

[54] LASER MAGNETIC IMMUNOASSAY METHOD AND APPARATUS THEREFOR AND SUPERPARAMAGNETIC MATERIAL-LABELED BODY AND METHOD FOR THE MANUFACTURE OF SAME

[75] Inventors: Koichi Fujiwara, Mito; Hiroko Mizutani, Tokyo; Hiromichi Mizutani, deceased, late of Tokyo, by Hiroko Mizutani, legal representative; Shuichi Shibata, Mito; Koichi Arishima, Mito; Mitsutoshi Hoshino, Mito; Yasushi Hoshino, Yokosuka, all of Japan

[73] Assignee: Nippon Telegraph and Telephone Corporation, Tokyo, Japan

[21] Appl. No.: 875,529

[22] Filed: Apr. 27, 1992

Related U.S. Application Data

[63] Continuation of Ser. No. 342,956, Apr. 25, 1989, abandoned.

[30] Foreign Application Priority Data

Apr. 26, 1988 [JP] Japan .................. 63-102914
Apr. 20, 1989 [JP] Japan .................. 1-101311

[51] Int. Cl.$^5$ ............ C12Q 1/70; G01N 33/553
[52] U.S. Cl. .................... 435/5; 422/82.05; 422/82.09; 435/7.23; 435/7.24; 435/7.32; 436/526; 436/805; 436/806; 436/813; 436/817; 356/337
[58] Field of Search ........... 436/526, 64, 63, 805, 436/806, 824, 518, 813, 817; 435/5, 29.34, 7.23, 7.24, 7.32; 422/68.1, 69, 82.05, 82.09, 73; 209/213, 215, 223.1, 223.2; 210/222, 695; 356/337-340, 345, 369

[56] References Cited

U.S. PATENT DOCUMENTS

| | | |
|---|---|---|
| 3,970,518 | 7/1976 | Giaever . |
| 4,115,535 | 9/1978 | Giaever ................ 436/526 |
| 4,177,253 | 4/1979 | Davies et al. . |
| 4,297,337 | 10/1981 | Mansfield et al. ........ 436/526 |
| 4,452,773 | 6/1984 | Molday . |
| 4,454,234 | 6/1984 | Czerlinski . |
| 4,582,622 | 4/1986 | Ikeda et al. . |
| 4,672,040 | 6/1987 | Josephson ............ 436/526 |
| 4,935,147 | 6/1990 | Ullman et al. ........... 435/2 |

FOREIGN PATENT DOCUMENTS

0125995 11/1984 European Pat. Off. .
62-118255 5/1987 Japan .

(List continued on next page.)

OTHER PUBLICATIONS

Molday et al., *Journal Of Immunological Methods*, "Immunospecific Ferromagnetic Iron-Dextran Reagents For The Labeling and Magnetic Separation of Cells", vol. 52, pp. 353-367, 1982, Netherlands.

*Primary Examiner*—Esther L. Kepplinger
*Assistant Examiner*—Susan C. Wolski
*Attorney, Agent, or Firm*—Frishauf, Holtz, Goodman & Woodward

[57] ABSTRACT

A laser magnetic immunoassay (LMIA) technique is presented which combines the high detection sensitivity of the radioimmunoassay (RIA) technique with the simplicity of particle agglutination (PA) technique. The LMIA technique dispenses with the separation step of bound and free species (B/F separation), yet provides detectivity of the order of picogram of viral species per milliliter of analyte solution. The procedure includes of the steps of: preparing a superparamagnetic-labeled body of antigen or antibody; subjecting a specimen sample and the magnetic-labeled body to a specific immunoreaction to produce a reacted body; subjecting the reacted body containing both bound and free species to a spot magnetic field gradient; irradiating the spot with a laser beam; measuring the intensity of the outgoing light from the spot; and making a quantitative determination of the virus according to the time difference in the outgoing light signals generated by bound and free species.

5 Claims, 8 Drawing Sheets

FOREIGN PATENT DOCUMENTS

| | | |
|---|---|---|
| 62-287159 | 12/1987 | Japan . |
| 63-79070 | 4/1988 | Japan . |
| 63-106559 | 5/1988 | Japan . |
| 63-108265 | 5/1988 | Japan . |
| 63-188764 | 8/1988 | Japan . |
| 63-188766 | 8/1988 | Japan . |
| 63-315951 | 12/1988 | Japan . |
| 63-315952 | 12/1988 | Japan . |
| 64-29768 | 1/1989 | Japan . |
| 1-107151 | 4/1989 | Japan . |
| 1-109263 | 4/1989 | Japan . |
| 1-182755 | 7/1989 | Japan . |
| 1-272968 | 10/1989 | Japan . |
| 1-272969 | 10/1989 | Japan . |
| 1-272971 | 10/1989 | Japan . |
| 1-272972 | 10/1989 | Japan . |
| 1-272973 | 10/1989 | Japan . |
| 1-321362 | 12/1989 | Japan . |
| 1-321363 | 12/1989 | Japan . |
| WO87/02063 | 4/1987 | PCT Int'l Appl. . |
| WO88/02188 | 3/1988 | World Int. Prop. O. . |

DIRECTION OF
MAGNETIC FIELD

LASER MAGNETIC IMMUNOASSAY METHOD AND APPARATUS THEREFOR AND SUPERPARAMAGNETIC MATERIAL-LABELED BODY AND METHOD FOR THE MANUFACTURE OF SAME

This application is a continuation of application Ser. No. 07/342,956, filed Apr. 25, 1989, now abandoned.

BACKGROUND OF THE INVENTION

1. Field of the Invention

The present invention relates to a laser magnetic immunoassay method utilizing an antigen-antibody reaction and apparatus therefor, which enables quantitative measurement of a specified antigen or antibody in a very small amount of a sample. It relates also to a superparamagnetic material-labelled substance for use in such method and apparatus and to a method for the manufacture of same.

2. Prior Art

Development of immunoassay methods utilizing an antigen-antibody reaction is now being made on a global scale as an early detection method for new virus-based diseases such as AIDS and adult T-cell leukemia, as well as various cancers.

Examples of micro-immunoassay methods utilizing hitherto known primary reaction that have been put in practice include radioimmunoassay (RIA), enzyme-immunoassay (EIA), fluorescence-immunoassay (FIA), etc. These methods use antigens or antibodies which are labeled with an isotope, an enzyme or a fluorescent substance in order to detect the presence or absence of corresponding antibodies or antigens, respectively, that react specifically therewith.

Although the RIA has high sensitivity for detection, it has many restrictions in its practice because it uses radioactive substances as a label substance. EIA and FIA, both of which have less restrictions and thus are easier to practice than RIA, have low sensitivity for detection and are difficult to give accurate quantitative measurements.

In order to overcome the defects of the above-described immunoassay methods, the present inventors previously studied laser immunoassay methods which were based on different principle than the above-described methods and proposed laser magnetic immunoassay methods and apparatuses, and also methods for the preparation of specimens as described in WO/88/02118 (PCT/JP87/00694 corresponding to Japanese Patent Application Nos. 61-224567, 61-252427, 61-254164, 62-22062, 62-22063, 62-152791, 62-152792, and 62-184902), and Japanese Patent Application Nos. 62-264319, 62-267481, 63-6050, 63-102912, 63-102913, 63-102915, 63-102917, 63-102918, 63-156519, and 63-156520. In the laser magnetic immunoassay methods according to the prior proposals, magnetically labeled specimens are concentrated locally at a desired position or point of concentration in a gradient magnetic field using magnetic micro-particles and the laser beam is irradiated to the local concentration point to generate an output beam or light from the specimen such as interfered light, scattered light, transmitted light, diffracted light, etc., which is then detected by appropriate detecting means. The methods enable ultra-micro detection in the order of picograms without using isotopes.

In the laser magnetic immunoassay method as described above, a magnetic-labeled body or substance, which is composed of a micro-particle as a label and an antigen or antibody attached thereto, and an antibody or antigen, respectively, as a specimen or sample are subjected to antigen-antibody reaction to form a magnetic-labeled immunocomplex (or a magnetic-labeled body-specimen complex, as used in the previous applications), which is then separated and removed from unreacted magnetic-labeled body using magnetic force or centrifuging, followed by detection of the magnetic-labeled immunocomplex. The operation of separation and removal is relatively cumbersome and it will be very advantageous if it is possible to recognize only magnetic-labeled immunocomplexes.

Generally, labeling methods practically used nowadays including the above-described laser magnetic immunoassay method as well as RIA, EIA, FIA, etc., accompany troublesome washing step which must be repeated many times in spite of improved detection sensitivity. On the other hand, a micro-particle aggregation method (PA), which is one of the non-labeling methods, is disadvantageous in that it has a low sensitivity for detection in spite of the fact that the adjustment or preparation of specimens is simple and easy.

It is therefore very advantageous if labeling methods can be performed without separating and removing unreacted labeling materials and only specimens can be detected selectively.

Other examples of conventional non-separating type immunoassay methods utilizing magnetic micro-particles include the following ones.

(1) Toshimitsu Musha, Japanese Patent Application No. 60-257545, "Method for Detecting Immune Reaction Using Magnetic Field" describes a method in which polarized radiation is radiated onto magnetic micro-particles while they are being dislocated due to a change in the magnetic field and the occurrence of an immune reaction is detected by detecting the change in the plane of the polarization of scattered light generated upon antigen-antibody reaction of the micro-particles. The publication describes the measurement method itself in detail but fails to describe examples as to how to apply it to an antigen-antibody reaction practically and sensitivity for detection or a like is unknown.

(2) Yukio Karube and Chiki Ishii, Japanese Patent Application No. 61-130506, "Method for Measuring the Concentration of Antigens and Antibodies", and Japanese Patent Application No. 61-235841, "Suspension of Antigen- or Antibody-Immobilized Magnetic Micro-particles and Method for Measuring the Concentration of Antigen and Antibodies Using Such Suspension" relate to measurements in which an antigen-antibody-magnetic micro-particle combination is produced under the application of a magnetic field, and then application of the magnetic field is stopped and magnetic micro-particles to which unreacted antibodies or antigens are immobilized are dispersed in a sample solution followed by measuring the concentration of the agglutinate suspended in the sample solution. The sensitivity for detection of this method is about 50 micrograms/milliliter. The detection sensitivity of this assay method is about 6 digits lower than that of the method of the present invention described hereinbelow.

Next, earlier proposals on magnetic labeling materials for use in the separation of cells or in the transfer of medicines are summarized below.

(3) Giaever, U.S. Pat. No. 3,970,518, "Magnetic Separation of Biological Particles", discloses a method of separating cells or the like by coating ferromagnetic or ferrimagnetic materials such as ferrite, perovskite, chromite, magnetoplumbite, etc. having a size in the range between the size of colloid particles and 10 micrometers with an antibody.

(4) Davies, et al., U.S. Pat. No. 4,177,253, "Magnetic Particle for Immunoassay", describes composite magnetic particles having a particle size of 1 micrometer to 1 cm and comprising a core material of a low density coated on the surface thereof with a metal magnetic-material such as Ni, etc., and a biologically active substance such as an antigen or antibody.

(5) Molday, U.S. Pat. No. 4,452,773, "Magnetic Iron-Dextran Microspheres", describes dextran-coated micro-particles of magnetite, which is one of ferromagnetic substances having a particle size of preferably 30 to 40 nm.

(6) Czerlinski, U.S. Pat. No. 4,454,234, "Coated Magnetizable Microparticles, Reversible Suspensions Thereof, and Processes Relating Thereto", describes magnetic micro-particles having a particle size in the range between the size of magnetic domain and about 0.1 micrometer and comprising micro-particles of a ferromagnetic material such as ferrite, yttrium-iron-garnet, etc. whose Curie temperature is in the range between 5 degree C. to 65 degree C. and whose surface is coated with a copolymer composition based on acrylamide.

(7) Ikeda, et al., U.S. Pat. No. 4,582,622, "Magnetic Particulate for Immobilization of Biological Protein and Process of Producing the Same", describes particles of a particle size of about 3 micrometers composed mainly of gelatin and containing 0.00001% to 2% ferromagnetic substance composed of ferrite.

(8) Margel, U.S. Pat. No. 4,324,923, "Metal Coated Polyaldehyde Microspheres", describes polyaldehyde microspheres coated with a transient metal and containing ferromagnetic substance such as iron, nickel, cobalt, etc. as a magnetic material.

The magnetic materials described in (4) to (8) above each are ferromagnetic or ferrimagnetic particles having a particle size of at least 30 nm, and are classified under as ferromagnetic materials. Ferromagnetic materials are those having a particle size of usually several tens nm or more, which may vary depending on the kind of the material, and showing residual magnetization after disappearance of an external magnetic field.

However, the proposals on the separation of cells and transfer of medicines are still being researched and most of which have not been put in practice.

SUMMARY OF THE INVENTION

An object of the present invention is to provide a new laser magnetic immunoassay method and an apparatus therefor having a detection sensitivity higher than that of RIA but involving a simple and easy preparation of specimens to be measured which have less restriction when put into practice.

Another object of the present invention is to provide a superparamagnetic-labeled body which can be used advantageously in such a laser magnetic immunoassay method, apparatus therefor, and a method for the preparation thereof.

Other objects and advantages of the present invention will be apparent from the following description with reference to the attached drawings.

DETAILED DESCRIPTION OF THE INVENTION

Figure 1:
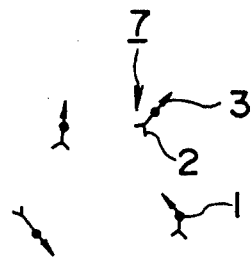
FIG. 1 is a schematic illustration of a superparamagnetic-labeled body dispersed in a dispersion medium.

According to a first embodiment, the present invention provides a laser magnetic immunoassay method comprising (a) a first step of subjecting a superparamagnetic-labeled body composed of a micro-particle of a superparamagnetic substance and an antigen or antibody attached thereto and an antibody or antigen, respectively, as a specimen to antigen-antibody reaction to form a superparamagnetic-labeled immunocomplex, (b) a second step of applying magnetic field to a solution containing the superparamagnetic-labeled immunocomplex, which is a complex between the superparamagnetic-labeled body and the specimen after the first step, to guide and concentrate the superparamagnetic-labeled immunocomplex to a predetermined position of concentration, and (c) a third step of distinguishing between unreacted superparamagnetic-labeled body and the superparamagnetic-labeled immunocomplex by a difference in time in which they reach the position of concentration.

According to a second embodiment of the present invention, a laser magnetic immunoassay method is provided in which the antigen-antibody reaction in the first step in the first embodiment is performed in a magnetic field to effect alignment of the direction of magnetization of the superparamagnetic-labeled immunocomplex obtained after the antigen-antibody reaction.

The superparamagnetic material used in the assay methods according to the first and second embodiments of the present invention described above is a substance which has a particle size smaller than that of a ferromagnetic material and retains no residual magnetization after disappearance of the external magnetic field. The superparamagnetic material and ferromagnetic material are quite different from each other in their hysteresis curve, susceptibility, Mesbauer effect, etc. Indeed, ferromagnetic materials are most suited for the conventional assay methods since they require that magnetic micro-particles used for labeling be efficiently guided even when a weak magnetic force is applied. On the other hand, in the non-separation assay method according to the first embodiment of the present invention, it is required that the magnetic-labeled body alone be difficult to guide by a magnetic force, and for this purpose superparamagnetic materials are most suited.

As for the antigen-antibody reaction, there can be used (i) a direct method in which a specimen and a superparamagnetic-labeled body are reacted directly, and (ii) a sandwich method in which at first a known antigen or antibody is immobilized onto the surface of a non-magnetic microsphere, and then after reacting the non-magnetic microsphere with a specimen, a superparamagnetic-labeled body is added to cause a reaction between the specimen and the superparamagnetic-labeled body.

In the first and second embodiments, the difference between the superparamagnetic-labeled body and the superparamagnetic-labeled immunocomplex in the period of time in which they reach the position of concentration can be detected and measured by radiating a laser beam to the position of concentration and detecting outgoing or output light such as scattered light, transmitted light, reflected light, interfered light, diffracted light, etc. from the position of concentration. Upon the detection, a method may be used in order to improve the detection sensitivity in which the signal component in synchronization with the sweep frequency of the laser beam is detected selectively. Alternatively, another method may be used in which in the second step, a laser beam is radiated both to the position of concentration and to that of nonconcentration simultaneously or serially in chronological order and outgoing light is detected, with the data from the position of nonconcentration being used as a reference for comparison to quantitatively determine the amount of the specimen.

According to a third embodiment of the present invention, a laser magnetic immunoassay apparatus is provided, which comprises a specimen container for holding-in a solution containing a superparamagnetic-labeled body composed of a micro-particle of a superparamagnetic substance and an antigen or antibody attached thereto, and a superparamagnetic-labeled immunocomplex, formed upon the antigen-antibody reaction between the superparamagnetic-labeled body and an antibody or antigen, respectively, as a specimen, a gradient magnetic field generating device for guiding and concentrating the superparamagnetic-labeled immunocomplex to a predetermined point, an incident light system for guiding laser beam to the position of concentration of the superparamagnetic-labeled immunocomplex in the specimen container, a light receiving system for receiving outgoing light from the superparamagnetic-labeled immunocomplex and that from the solution that contains no superparamagnetic-labeled immunocomplex, and a distinguishing means for distinguishing between the superparamagnetic-labeled immunocomplex and the unreacted superparamagnetic-labeled body.

As for the distinguishing means which can be used in the assay apparatus according to the third embodiment of the present invention it is preferred to employ an electronic circuitry which can detect or measure chronological change in the output light from the superparamagnetic-labeled immunocomplex after the reaction with comparing with chronological change in the output light from the unreacted superparamagnetic-labeled body. The gradient magnetic field generating device includes an electromagnet and a pole piece arranged opposite to the electromagnet so as to sandwich the specimen container together with the electromagnet. It is preferred that the electromagnet or the pole piece, or the specimen container be movable in a horizontal plane.

According to a fourth embodiment of the present invention, a superparamagnetic-labeled body is provided, which can be used as a labeled substance in the laser magnetic immunoassay method in accordance with the first and second embodiments described above and which comprises a superparamagnetic ultramicro particle, a coating layer composed of a biologically active substance coated on the surface of the superparamagnetic ultramicro particle, and an antigen or antibody immobilized onto the coating layer.

According to a fifth embodiment of the present invention, a method for the preparation of a superparamagnetic-labeled body is provided, which comprises providing ultramicro particles of a magnetic substance, forming a coating layer composed of a biologically active substance on the surface of the magnetic ultramicro particles, separating and collecting only those particles with the coating layer which show superparamagnetic property, and immobilizing an antigen or antibody onto the coating layer of the superparamagnetic ultramicro particles.

Needless to say, the superparamagnetic ultramicro particles used for the preparation of the superparamagnetic-labeled bodies described above have no problem of radioactivity and toxicity to humans and other inconveniences, and there is no particular restriction in their utilization in practice. The superparamagnetic ultramicro particles can be produced from any ferromagnetic substances, by rendering them ultramicro particles. The ferromagnetic substances can be selected appropriately, for example, from various compound magnetic substances such as magnetite and gamma-ferrite, metal magnetic substances such as iron, nickel and cobalt, etc.

The ferromagnetic substances can be converted into ultramicro particles using conventional methods excepting a mechanical grinding method, i.e., various gas phase methods and liquid phase methods. For example, an evaporation-in-gas method, a laser heating evaporation method, a coprecipitation method, etc. can be applied. The ultramicro particles produced by the gas phase methods and liquid phase methods contain both superparamagnetic particles and ferromagnetic particles in admixture, and it is therefore necessary to separate and collect only those particles which show superparamagnetic property. For the separation and collection, various methods including mechanical, chemical and physical methods can be applied, examples of which include centrifugation, liquid chromatography, magnetic filtering, etc. The particle size of the superparamagnetic ultramicro particles may vary depending upon the kind of the ferromagnetic substance used but it must be below the critical size of single domain particles. Preferably, it is not larger than 10 nm when the ferromagnetic substance used is magnetite or gamma-ferrite and it is not larger than 3 nm when pure iron is used as a ferromagnetic substance, for example.

The superparamagnetic ultramicro particles are coated on the surface thereof with a biologically active substance in order to immobilize an antigen or antibody thereon. Examples of the biologically active substance include sugars such as dextran, proteins such as protein A, and polymer membrane such as polymethyl methacrylate. The antigen or antibody is immobilized on the surface of the layer of the biologically active substance.

The superparamagnetic-labeled body can be stored for long period of time by freezing and drying it. When it is used as a labeled reagent, it may be dispersed in an aqueous solution to which a surfactant is added. Alternatively, the superparamagnetic-labeled body can be stored in a cold place in the form of a solution with adding a surfactant in order to prevent aggregation. Suitable examples of the surfactant include TWEEN 20 (TWEEN comprises polyethyleneoxide concentrates containing oleic and lauric acid)(Pharmacia AB) which can also be used as a washing solution in enzyme-linked immunoadsorbent assay (ELISA), or laurylamine which is used for dispersing a magnetite-magnetic colloid employed for observing magnetic domains in the Bitter diagram method, CELAKOR (sodium carboxymethylcellulose), or Driwell (Fuji Photo Film)(a surface activating agent used in photographic processing) used for removing water and drying photographic films.

As is well known, ferromagnetic particles are converted to superparamagnetic particles according as their particle size is reduced greatly since the direction of easy magnetization thereof becomes random due to the influence of thermal movement. Taking magnetite particles as an example, it is known that they are converted to a mixture of ferromagnetic particles and superparamagnetic particles when their particle size is reduced to 10 nm or less. The ferromagnetism and superparamagnetism can readily be distinguished by measuring their hysteresis curves or susceptibility, or by Mesbauer effects. That is, the coercive force of superparamagnetic substances is zero and their susceptibility decreases as their particle size decreases since the influence of the particle size on the susceptibility is reversed at the critical particle size at which ferromagnetism is converted to superparamagnetism. In ferromagnetism a Mesbauer spectrum of iron is divided into 6 lines in contrast to superparamagnetism in which two absorption lines appear in the center, which enables quantitative determination of superparamagnetism. The thermal magnetic relaxation time in which magnetization is reversed due to thermal agitation is calculated to be 1 second at a particle size of 2.9 nm and about $10^9$ seconds or about 30 years at a particle size of 3.6 nm in the case of ultramicro particles of iron at room temperature when no external magnetic field is applied. This clearly shows that difference in the particle size of only 1 nm results in drastic change in the magnetic property.

The superparamagnetic-labeled body used in the assay methods according to the first and second embodiments for the present invention can react specifically with specimens, i.e., target cells such as viruses or cancer cells as well as antibodies to catch the specimens and magnetically label them since they are composed of the above-described magnetic particles made of superparamagnetic substance as a core whose surface is coated with an antigen or antibody. The superparamagnetic-labeled body has a size by two digits smaller than target cells such as cancer cells or lymphocytes, and its size does not exceed that of viruses. Generally, the specimens have many sites for combining antigens or antibodies, and thus addition of superparamagnetic-labeled body in excess amount with respect to the specimens results in that a single virus, for example, is combined with a plurality of superparamagnetic-labeled body. This combination gives rise to both magnetic amplification effect and volume amplification effect, resulting in that superparamagnetic-labeled body, which is superparamagnetic before the antigen-antibody reaction, behaves like a ferromagnetic substance after being converted into a complex with a specimen by the antigen-antibody reaction.

Therefore, in the laser magnetic immunoassay methods according to the first and second embodiments of the present invention, it takes a long time for the superparamagnetic-labeled body used as a magnetic label to reach the position of concentration of the labeled body when subjected to concentration operation in a gradient magnetic field because the superparamagnetic-labeled body shows a superparamagnetic property and the direction of easy magnetization is random and superparamagnetic-labeled body is more susceptible to Brownian movement. On the other hand the superparamagnetic-labeled immunocomplex, which is a complex between the superparamagnetic-labeled body and a specimen, has a particle size larger than that of the superparamagnetic-labeled body and as a result it behaves like a ferromagnetic particle, resulting in that it is less susceptible to Brownian movement, which permits a superparamagnetic-labeled immunocomplex to reach the position of concentration in a gradient magnetic field in a short period of time. Thus, it is possible to distinguish between unreacted superparamagnetic-labeled body and superparamagnetic-labeled immunocomplex after the antigen-antibody reaction by the time difference in which they reach the position of concentration.

In the laser magnetic immunoassay methods according to the first and second embodiments of the present invention, therefore, use of a superparamagnetic-labeled body as a label enables a distinction between unreacted superparamagnetic-labeled body and superparamagnetic-labeled immunocomplex after the reaction by the difference in time in which they reach the position of concentration, and no operation is needed for separating superparamagnetic-labeled body and superparamagnetic-labeled immunocomplex from each other, which makes it possible to readily perform measurements at a detection sensitivity higher than RIA. Accordingly, it is also possible to perform an automatic quantitative determination of antigens or antibodies as a specimen according to the first and second embodiments of the present invention.

In addition, the superparamagnetic-labeled body used in the first and second embodiments above has a size not exceeding that of viruses and is by three digits smaller than that of lymphocytes or cancer cells, and when superparamagnetic-labeled body is used which has attached thereon a monoclonal antibody specific to lymphocytes infected with a virus, many superparamagnetic-labeled body bind with a single lymphocyte. This results in magnetic amplification. Furthermore, formation of a superparamagnetic-labeled immunocomplex from a lymphocyte and superparamagnetic-labeled bodies means a significant increase in size as compared with the superparamagnetic-labeled body itself. Thus a volume amplification effect is also observed. For this reason, although a detection limit in detecting superparamagnetic-labeled body alone by optically detecting scattered light, interfered light, reflected light, diffracted light, etc. is about $1 \times 10^{-12}$ g, it is improved by one digit or more as the result of the amplification effects. Therefore, the assay methods according to the first and second embodiments of the present invention permits detection of a single virus or lymphocyte.

The alignment of the direction of the easy magnetization of superparamagnetic-labeled immunocomplex during the antigen-antibody reaction in the first step renders the complex after the antigen-antibody reaction ferromagnetic, which makes it possible to guide and concentrate the complex to the position of concentration efficiently in a short period of time.

Furthermore, the laser magnetic immunoassay apparatus according to the third embodiment of the present invention allow the immunoassay methods according to the first and second embodiments advantageously.

As the results of further research by the present inventors, it has now been found that magnetic-labeled immunocomplexes can be distinguished from unreacted magnetic-labeled bodies even when ferromagnetic micro-particles are used as a label.

Therefore, a sixth embodiment of the present invention provides a laser magnetic immunoassay method, which comprises providing specific magnetic-labeled specimen utilizing antigen-antibody reaction, radiating laser beam on the magnetic-labeled specimen, and detecting and measuring outgoing light from the specimen, wherein the method further comprises applying a unidirectional gradient magnetic field which is increasing linearly in one direction to a solution containing a mixture of unreacted magnetic-labeled body, a specimen and a magnetic-labeled immunocomplex which is a complex between the specimen and the magnetic-labeled body after antigen-antibody reaction, and distinguishing and quantitatively determining the magnetic-labeled immunocomplex in the solution by means of a difference in magnetophoretic ability between the unreacted magnetic-labeled body and the immunocomplex.

As the label substance for the magnetic-labeled body used in the sixth embodiment of the present invention, there can be used both superparamagnetic substances and ferromagnetic substances.

According to a seventh embodiment of the present invention, a laser magnetic immunoassay apparatus is provided, which comprises a gradient magnetic field generating device for generating unidirectional gradient magnetic field, a magnetophoretic tube placed inside the gradient magnetic field generating device, an incident optical system for guiding a laser beam from a laser beam source to a predetermined position on a higher magnetic field side of the magnetophoretic tube, a output optical system for receiving outgoing light from a magnetic-labeled immunocomplex, an electronic circuitry for analyzing time response characteristics of the outgoing light, a first injecting means for injecting a mixed solution containing a specimen and a magnetic-labeled body after being subjected to antigen-antibody reaction in an inlet on a lower magnetic field side of the magnetophoretic tube, and a second injecting means for injecting a non-magnetic solvent in the magnetophoretic tube after washing, whereby permitting distinction and quantitative determination of the magnetic-labeled immunocomplex in the mixed solution containing the unreacted magnetic-labeled body and the magnetic-labeled immunocomplex.

The measurement of the outgoing light from the magnetic-labeled specimen can be performed using scattered light, transmitted light, reflected light, interfered light, or diffracted light.

The principle on which the sixth embodiment of the present invention is based will be explained in detail hereinbelow.

Generally, when magnetic field is applied to a magnetic substance placed in a static solution, the magnetic substance tends to move toward the position with the highest magnetic field due to attraction by magnetic force. The equation of motion of the magnetic substance can be described as follows.

$$\vec{J} = n \cdot \frac{Fm}{6\pi\eta\left(\frac{a}{2}\right)} - \frac{kT}{6\pi\eta\left(\frac{a}{2}\right)} - \text{grad } n$$

$$\text{div } \vec{J} + \frac{\partial n}{\partial t} = 0$$

wherein $\vec{J}$ indicates flow of the magnetic substance, n stands for density of the magnetic substance, Fm stands for magnetic force ($Fm = \frac{1}{2} \cdot v\chi \text{grad} H^2$ in which v is volume of the magnetic substance, $\chi$ is susceptibility, and H is magnetic field), $\eta$ is viscosity, a is diameter of the magnetic substance, k is Boltzmann constant, and T is absolute temperature.

The motion of the magnetic substance is influenced by the intensity of external magnetic field, the temperature and viscosity of the solution, the magnetic momentum, density, and particle size of the magnetic substance. Magnetic force is proportional to the product of the volume and susceptibility of the magnetic substance. Therefore, when the particle size of the ferromagnetic micro-particles is reduced to a very small value, the direction of easy magnetization of the particles become random due to thermal movement, and phase transfer from ferromagnetism to superparamagnetism. In the case of magnetite, for example, the change from ferromagnetism to superparamagnetism occurs when the particle size is 10 nm or less. When a solution containing a superparamagnetic-labeled body alone is located in a unidirectional gradient magnetic field, it takes a long time for the superparamagnetic-labeled body to gather at the position where magnetic field is highest because of intense Brownian movement. In contrast, a superparamagnetic-labeled immunocomplex formed upon antigen-antibody reaction between the specimen and the superparamagnetic-labeled body has a particle size larger than the superparamagnetic-labeled body, and therefore the Brownian movement thereof is not so intense. Thus, when a superparamagnetic-labeled immunocomplex is placed in a gradient magnetic field for concentration, it is concentrated in a shorter period of time than superparamagnetic-labeled bodies are. The immunoassay method according to the first embodiment of the present invention described hereinbefore utilizes the above-described phenomenon.

On the other hand, when the magnetic substance used is a ferromagnetic substance, the influence of Brownian movement is not so serious but instead the magnetic momentum of the magnetic substance and the viscous drag by the solution when the magnetic substance travels therein magnetophoretically become overwhelming. Stated otherwise, the principle on which the laser magnetic immunoassay method according to the sixth embodiment of the present invention is based is to distinguish between the superparamagnetic-labeled immunocomplex and the unreacted superparamagnetic-labeled body by transient characteristics of magnetophoresis taking notice of the difference between the two in the magnetic momentum and viscous drag. Needless to say, both the magnetic-labeled particles are hardly distinguishable between them once a steady state is reached after completion of magnetophoresis since both of them gather at the position where the magnetic field is highest.

The method according to the sixth embodiment is useful not only in a so-called direct method in which a specimen and the above-described superparamagnetic-labeled body are directly subjected to antigen-antibody reaction, but also in a so-called sandwich method in which a known antigen or antibody is immobilized onto the surface of non-magnetic microspheres and after subjecting the non-magnetic microspheres and a specimen to antigen-antibody reaction, the above-described superparamagnetic-labeled body to cause an antigen-antibody reaction between the specimen and the superparamagnetic-labeled body.

Furthermore, the immunoassay method according to the sixth embodiment of the present invention can be practiced advantageously using the immunoassay apparatus according to the seventh embodiment of the present invention.

With the above-described features of the present invention, steps of washing and separating unreacted magnetic-labeled body can be omitted which were unavoidable in the conventional RIA, EIA, and FIA and earlier proposals by the present inventors on the laser magnetic immunoassay methods. The present invention thus facilitates automation of immunoassay without decreasing detection sensitivity.

According to the present invention, tests for antigen-antibody reaction with high detection sensitivity can be performed efficiently without separating unreacted magnetic-labeled body from magnetic-labeled immunocomplex. In addition, the magnetic micro-particles used as a label have no problem as to radioactivity and toxicity, and those stable to specimens are available without difficulty.

The laser magnetic immunoassay apparatuses according to the present invention can be used in cell diagnosis for detecting cancer cells, etc. and antibody tests for various infectious diseases as well as direct detection of viruses. They can also be used in the measurement of various hormones such as peptide hormones or various enzymes, vitamins, drugs, etc. where RIA has heretofore been applied widely. As the result, accurate measurements, which have hitherto been impossible to perform unless run in a limited installation using a RIA, can now be practiced widely in ordinary environment.

Furthermore, since the laser magnetic immunoassay methods and apparatuses of the present invention are suited for automation of antigen-antibody reaction tests, they exhibit particular effects when they are used in screening tests and close examinations of various viruses, cancers and the like which are necessary in group examination. As stated above, the present invention can be put to use in early diagnosis and therapy and thus makes a great contribution in the field of medical treatment.

EXAMPLES

Referring to the attached drawings and examples the present invention will be described in greater detail.

EXAMPLE 1

Laser Magnetic Immunoassay Method According to the First Embodiment

Referring to FIGS. 1 to 4, reference numeral 1 indicates micro-particles of a superparamagnetic substance, 2 an antibody, 3, an arrow indicating the direction of easy magnetization of the micro-particles of the superparamagnetic substance, 4 an antibody, 5 a non-magnetic microsphere, 6 a virus (antigen), 7 a superparamagnetic-labeled body, 8 a non-magnetic-substance-antibody complex, 9 a superparamagnetic-labeled immunocomplex, 10 an incident laser beam, 11 an outgoing light, 12 a pole piece, 13 a specimen container, and 14 an electromagnet.

The superparamagnetic ultramicro-particles 1 are ultramicro-particles of iron having a mean particle size of 2 nm, whose surface is coated with protein A. The iron ultramicro-particles were prepared by conventional vacuum evaporation method, and a magnetic field filter was used to separate those particles with superparamagnetic property from those with ferromagnetic property in order to recover only superparamagnetic particles.

As shown in FIG. 1, the antibody 2 composed of IgG (immunoglobulin) was immobilized to protein A coated on the surface of the superparamagnetic ultramicro-particle 1 to obtain the superparamagnetic-labeled body 7. The antibody 2 was immobilized by reacting protein A with a rabbit hyperimmune serum to influenza virus (B/IBARAGI/2/85).

Figure 2:
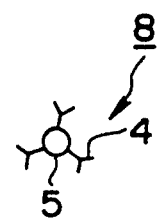
FIG. 2 is a schematic illustration of an antibody immobilized onto the surface of a non-magnetic microsphere.

On the other hand, as shown in FIG. 2, the antibody 4 composed of an IgG similar to the antibody 2 was adsorbed on the surface of the non-magnetic microsphere 5 made of an acrylic polymer having a particle size of 1 micrometer after activation of the surface to obtain the non-magnetic substance-antibody complex 8.

Figure 3:
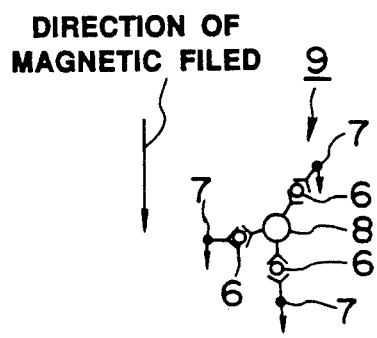
FIG. 3 is a schematic illustration of a superparamagnetic-labeled immunocomplex in a state in which its direction of easy magnetization is aligned during an antigen-antibody reaction by means of a magnetic field applied thereto.

Then, as shown in FIG. 3, influenza virus 6 found in a gargling water from a patient was used as a specimen. Antigen-antibody reaction was carried out in a solution containing the virus 6, the superparamagnetic-labeled body 7 and non-magnetic substance-antibody complex 8. During the reaction, a strong magnetic field was applied to align the direction of easy magnetization of the immunocomplex 9, which was a complex composed of the labeled body 7, the non-magnetic substance-antigen complex 8 and the virus 6, to convert the immunocomplex 9 ferromagnetic.

Figure 4:
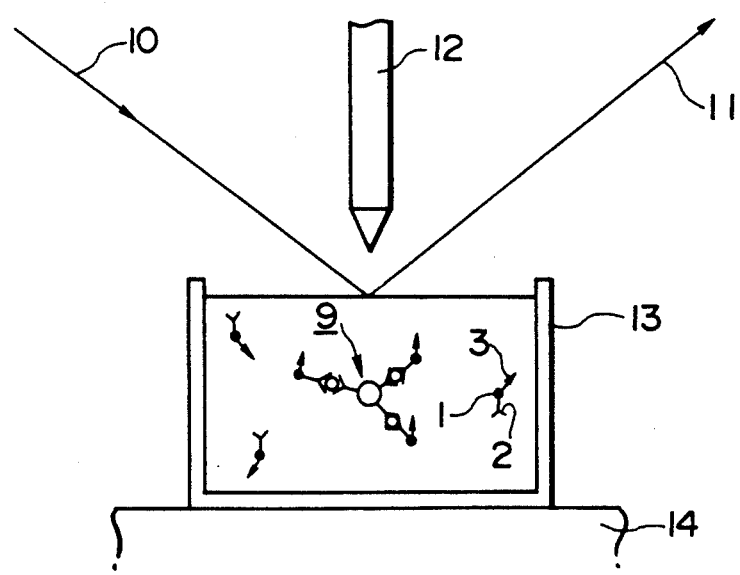
FIG. 4 is a schematic diagram illustrating a step of concentrating and detecting the complex as shown in FIG. 3.

Next, a solution containing the immunocomplex 9 was charged in the specimen container 13. As shown in FIG. 4, the specimen container 13 is sandwiched by the pole piece 12 made of pure iron and the electromagnet 14 opposing to each other. The pole piece 12 is in the form of a rod having a diameter of 8 mm with the tip thereof facing the water surface in the specimen container being sharpened so that a gradient magnetic field can be generated by the pole piece 12 and the electromagnet 14, which together constitute a gradient magnetic field generating device, such that the magnetic field just below the pole piece 12 is highest. The immunocomplex 9 was guided and concentrated on the surface of the liquid in the specimen container just below the pole piece 12 using the gradient magnetic field. Then, an incident He-Ne laser beam 10 having a wavelength of 632.8 nm was radiated to the position of concentration, and scattered light therefrom was detected as the outgoing light 11. Upon chronological detection of the outgoing light 11, the immunocomplex 9 which reached the position of concentration in a short period of time was clearly distinguished from the unreacted superparamagnetic-labeled body 7 which reached the position of concentration in a long period of time. When transmitted light, reflected light, interfered light, or diffracted light was, selected as output light, the labeled body 7 and the immunocomplex 9 were distinguished similarly.

EXAMPLE 2

Laser Magnetic Immunoassay Apparatus According to Third Embodiment

Figure 5:
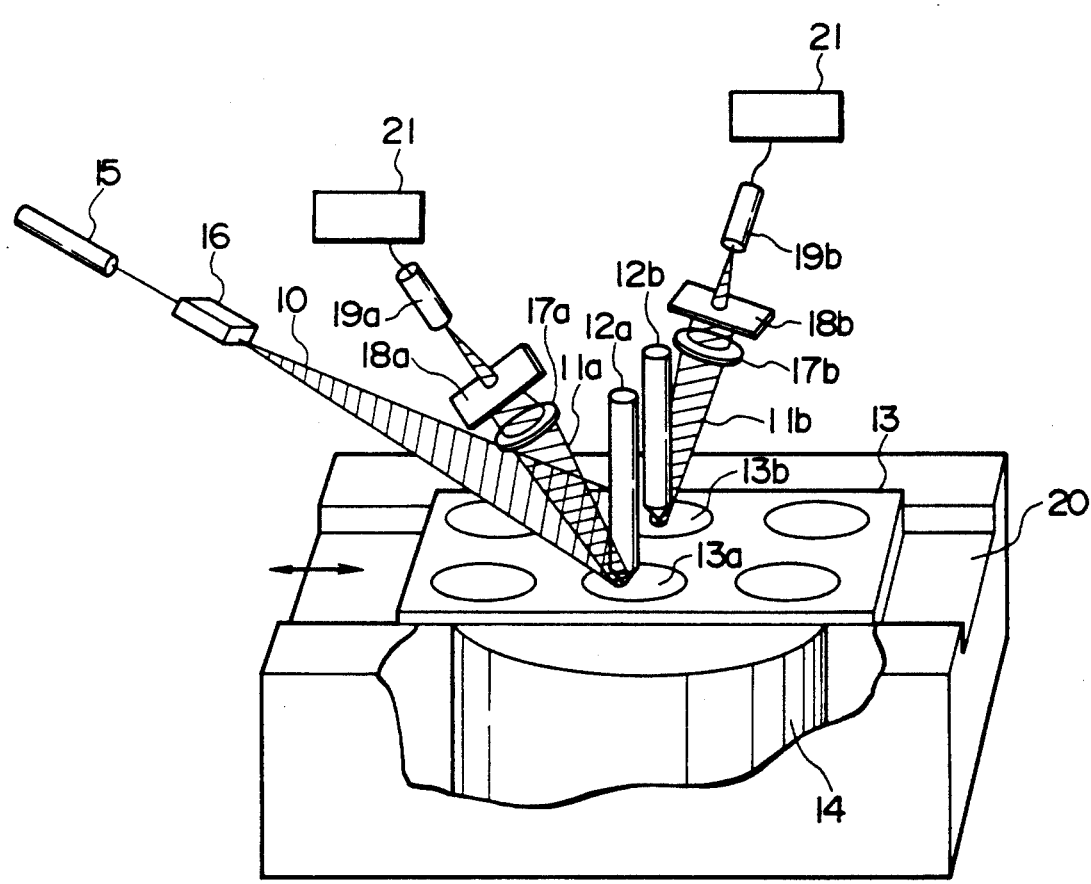
FIG. 5 is a perspective of a laser magnetic immunoassay apparatus according to an embodiment of the present invention.

Referring to FIG. 5, an example of apparatus which can suitably practice the immunoassay method according to the first embodiment of the present invention will be described hereinbelow.

In FIG. 5, reference numeral 10 indicates an incident light flux, 11a and 11b scattered light fluxes, 12a and 12b pole pieces, 13 a specimen container, 13a and 13b wells of the specimen container 13, 14 and electromagnet, 15, a laser beam source, 16 a deflector, 17a and 17b a condenser lens, 18a and 18b slit plates, 19a and 19b photomultipliers, 20 a horizontal dislocation device for driving the specimen container 13, and 21 an electronic circuitry constituting distinction means.

The laser beam source 15 is fitted at an angle of 30 degrees (°) with respect to horizontal plane so that the incident laser beam flux 10 from the laser beam source 15 can sweep in a plane with the deflector 16 to radiate both the wells 13a and 13b serially. The pole pieces 12a and 12b are arranged just above the positions of radiation on the wells 13a and 13b, respectively. The scattered light fluxes 11a and 11b travel through the condenser lenses 17a and 17b, respectively, and then the slits of the plates 18a and 18b, respectively, and are detected by the respective photomultipliers 19a and 19b. A solution containing the immunocomplex 9 was charged in the wells 13a and 13b and the scattered light fluxes 11a and 11b were detected by the photomultipliers 19a and 19b, respectively, and analyzed by the electronic circuitry 21. Thus, measurement of two specimens was performed efficiently. By serially moving the specimen container 13 using the horizontal dislocation device 20, measurement of many specimens was successful. Comparative measurement was also enabled by charging a specimen in one of the wells 13a and 13b and a specimen control in another.

It is also possible to split the incident laser beam flux 10 with a beam splitter so that a plurality of wells can be radiated simultaneously. Needless to say, the split beams should be radiated to areas including the respective positions of concentration. In addition, it is preferred to insert the deflector 16 immediately before beam splitting and sweep the position of concentration and the position of non-concentration for the wells 13a and 13b in order to remove the influence by background light. Lock-in amplification of signals from the specimen which are in synchronization with the sweep frequency results in further improvement in S/N ratio.

Figure 6:
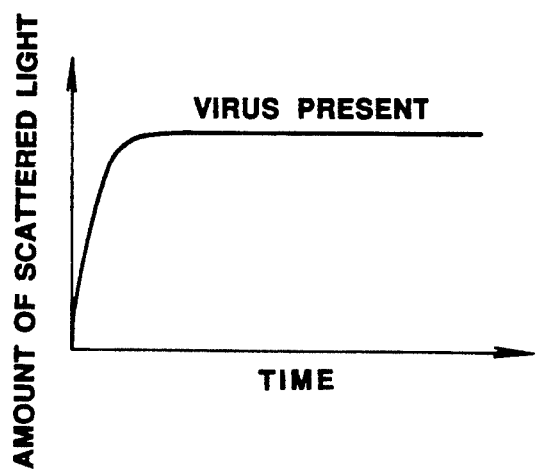
FIG. 6 is a graph showing results of measurements obtained using the apparatus shown in FIG. 5, showing time dependency of the amount of scattered light when a specimen is present.
Figure 7:
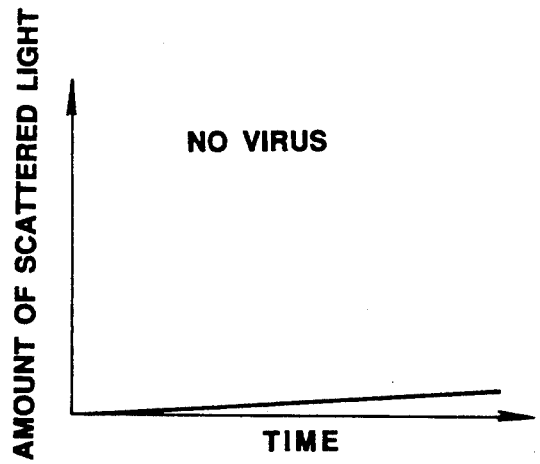
FIG. 7 is a graph showing results of measurements obtained using the apparatus shown in FIG. 5, showing time dependency of the amount of scattered light when no specimen is present.

FIGS. 6 and 7 are graphs showing an example of results obtained upon measurement performed using the laser magnetic immunoassay apparatus of the present invention. More particularly, FIG. 6 shows the chronological change in the amount of scattered light when a specimen, i.e., virus, is present, and FIG. 7 shows similar data in the case where no virus is present but the same treatments in the magnetic field were performed. The measurement of the amount of scattered light was carried out by a method in which the outputs of the photomultipliers 19a and 19b were amplified with a lock-in amplifier and signals synchronized with the sweep frequency of the incident laser beam flux 10 were recorded. When a specimen was present the amount of the scattered light from the specimen immediately increased to a constant value as soon as the electromagnet was energized. In contrast, the amount of the scattered light from the specimen control increased only a little with lapse of time.

As described above, only specimens can be determined quantitatively by detecting a chronological change in the amount of scattered light and subtracting therefrom the amount of the scattered light from the specimen control. There is no need to simultaneously measure specimen controls for every specimen but it is possible to measure a single specimen control before the measurement of specimens and recording results on a memory device.

Measurement of influenza virus using the apparatus described above resulted in that the influenza virus, which otherwise needed cultivation of virus prior to detection, was able to be detected directly without incubation, and that various influenza viruses were measured in amounts of about 10 individuals in a gargling water from a patient. In contrast, a conventional RIA was unable to perform detection unless virus were present in a population of several thousands/milliliter or more.

EXAMPLE 3

Another Example of a Laser Magnetic Immunoassay Method According to First Embodiment An antigen-antibody reaction between a virus and a magnetic-labeled body was performed by a direct method.

Superparamagnetic ultramicro-particles used as a label were magnetite ultramicro-particles having a mean particle size of 9 nm whose surface was coated with dextran. The magnetite ultramicro-particles were prepared with reference to the method by Molday et al. (J. Imm. Meth., 52. p. 353–367, 1982) and were centrifuged followed by collecting supernatant in order to remove ferromagnetic particles. Then, IgG antibody isolated from rabbit hyperimmune serum to influenza virus was covalently bonded to the dextran coated on the surface of the thus-obtained ultramicro-particles to obtain superparamagnetic-labeled body. Conventional liquid chromatography and magnetic filter may also be used alone or in combination in order to separate the superparamagnetic substance from the ferromagnetic substance.

Next, $1 \times 10^{-8}$ g of the above-described superparamagnetic-labeled body was added to 1 ml of a specimen collected from a gargling water from a patient, and the specimen and the superparamagnetic-labeled body were subjected directly to antigen-antibody reaction to obtain a superparamagnetic-labeled immunocomplex. The immunocomplex was measured by the interference method described in WO/88/02118 (PCT/JP87/00694), "Laser Magnetic Immunoassay Method and Apparatus" filed by the present inventors. That is, outgoing light from the immunocomplex was projected onto a screen after 30 seconds from the excitation of the electromagnet in the gradient magnetic field generating device, and the projected image of interference fringes was observed.

Figure 14:
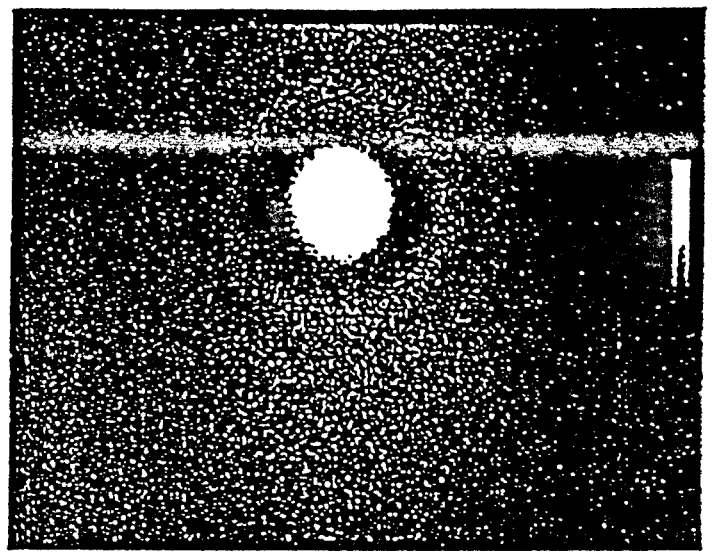
FIG. 14 is a picture drawing showing an image of interference fringes generated by a specimen (influenza virus) obtained in Example 3.
Figure 15:
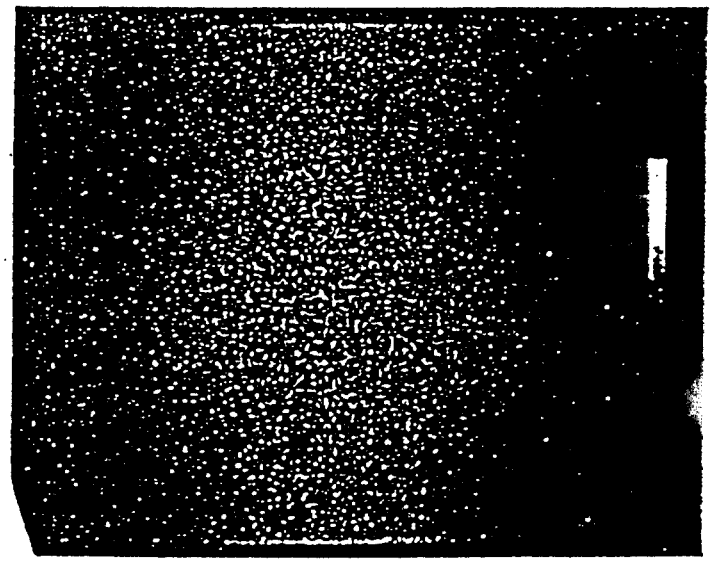
FIG. 15 is a picture drawing showing an image of interference fringes generated by a control specimen.

Interfered light from the specimen (virus) showed clear interference fringes (FIG. 14) from which the population of virus was presumed to be about 10 individuals/ml and that from the specimen control which contained no specimen (virus) showed only a little interference fringes (FIG. 15) from which it was judged that no virus was present.

This difference in interference fringes is believed due to difference in the degree of concentration, which is ascribable to the fact that on one hand, the size of the virus is 120 nm, on the other hand, that of the superparamagnetic-labeled body is about 9 nm, and thus the superparamagnetic-labeled immunocomplex has a size by about one digit larger than that of the superparamagnetic-labeled body. As stated above, it takes a longer time to concentrate the superparamagnetic-labeled body because of vivid Brownian movement in contrast to the superparamagnetic-labeled immunocomplex on which magnetic attraction by the gradient magnetic field influences more than Brownian movement does.

As a variation, the antigen-antibody reaction between the specimen and the superparamagnetic-labeled body was carried out in magnetic field of 10 kG, and then measurement was made by the same interference method as described above. As the result, the interference fringe of the specimen control appeared in the same manner as in the case where the antigen-antibody reaction was performed without applying the magnetic field, but the interference fringes of the specimen appeared faster than the case where the antigen-antibody reaction was performed without the application of the magnetic field, thus achieving reduction in the time of measurement.

For comparison, ferromagnetic particles of magnetite having a mean particle size of 50 nm, which had been bound to an antibody to virus in the same manner as described above were used as a magnetic-labeled body and similar experiment to the above was repeated. In this case, no difference was observed in the time of concentration between the magnetic-labeled immunocomplex and the unreacted magnetite ferromagnetic-labeled body, and the specimen was unable to distinguish.

The measurement means which can be used in the laser magnetic immunoassay method of the present invention is not limited to the above-described interference method. It is also possible to select conditions for measurement (magnetic field, time, etc.) which facilitate the distinction between the immunocomplex and the unreacted superparamagnetic-labeled body with respect to the outgoing light from the specimen and perform measurement of the amount of scattered light, transmitted light, reflected light or a like after a predetermined period of time from the excitation of the electromagnet.

EXAMPLE 4

In order to examine the applicability of the laser magnetic immunoassay method of the present invention to detection of leukemia and cancers, a model experiment for detecting target cells was practiced. To attach acryl resin particles of a particle size of 3 μm ("TORESPHERE", (non-magnetic microparticles made of acrylic resin) trade name for a product by Toray Limited) target cells, the surface of the acryl resin particles was activated, and sensitized with an ether-treated influenza virus as an antigen. As the superparamagnetic-labeled body was used the magnetite superparamagnetic-particles. The antigen-sensitized particles and the superparamagnetic-labeled body were subjected to direct antigen-antibody reaction, and measurement was performed by the interference method without separating unreacted superparamagnetic-labeled body. As the result, it was confirmed that the antigen-sensitized particles were distinguishable even by a single particle. Therefore, the laser magnetic immunoassay methods according to the first and second embodiments can be applied to the early diagnosis of T-lymphocytes and extraordinary cells such as cancer cells

EXAMPLE 5

Figure 8:
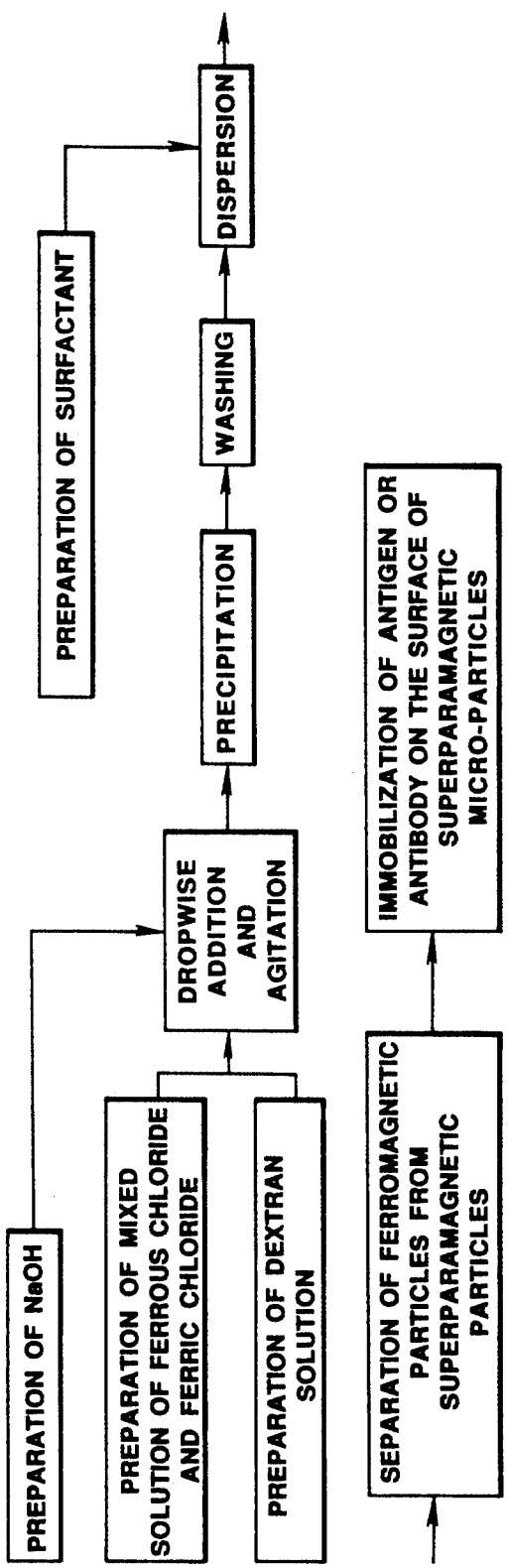
FIG. 8 is a schematic diagram showing an example of a method for the preparation of a superparamagnetic-labeled body according to another embodiment of the present invention.

Apparatus Suitable for Practicing Laser Magnetic Immunoassay Method According to First and Second Embodiment FIG. 8 illustrates the procedures of preparing superparamagnetic-labeled body according to the fifth embodiment of the invention.

In distilled water were dissolved 2.0 g of ferrous chloride ($FeCl_2.4H_2O$) and 5.4 g of ferric chloride ($FeCl_3.6H_2O$) and 50 ml of a 50% aqueous solution of dextran was added to the solution. A solution of NaOH in a concentration of 5 g/50 ml was added slowly to the resulting solution kept at 85° C. at a rate of 25 ml/minute while agitating the solution. After the settling of the precipitation formed supernatant was discarded. This washing operation was repeated 8 times. Then, a 0.5% aqueous solution of Tween 20 (Pharmacia AB)

was added as a dispersion stabilizer to the solution to make 100 ml in total. The solution was poured into centrifugation tubes each in an amount of 10 ml, and centrifuged at a speed of 20,000 rpm for 30 minutes. The precipitate containing ferromagnetic substances was discarded, and superparamagnetic ultramicro-particles were obtained from the supernatant. The superparamagnetic ultramicro particles thus obtained had a mean particle size of 9 nm, and were coated with dextran on the surface thereof.

Influenza virus IgG antibody isolated from rabbit serum was added to a solution having dispersed therein the superparamagnetic ultramicro-particles and subjected to covalent bonding to give superparamagnetic body.

A suspension liquid having suspended therein the superparamagnetic-labeled body (0.1 ml) adsorbed 40 HA of influenza virus.

EXAMPLE 6

Figure 9:
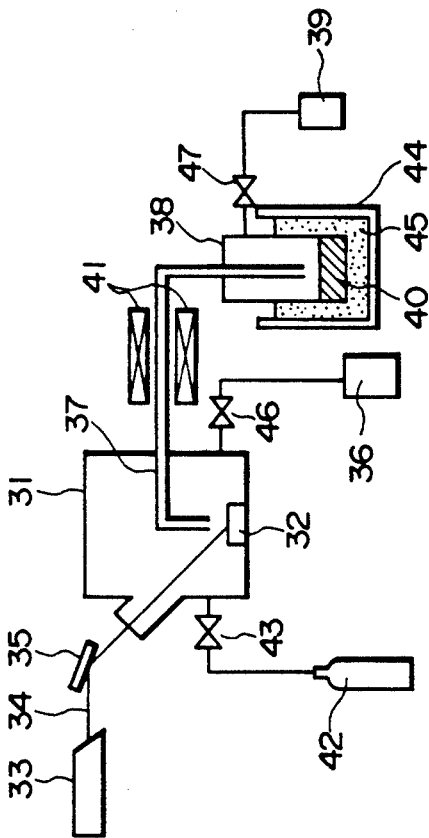
FIG. 9 is a schematic diagram, partially in cross-section, of an apparatus used advantageously in practicing a method for the preparation of a superparamagnetic-labeled body according to an embodiment of the present invention.

FIG. 9 shows an example of apparatus which can be used advantageously in practicing the method for preparing superparamagnetic-labeled body according to the present invention. In FIG. 9, reference numeral 31 indicates an atmospheric vessel, 32 a starting material for preparing superparamagnetic ultramicro-particles, 33 a laser beam source, 34 a laser beam, 35 a mirror, 36 a vacuum pump, 37 a collecting tube for collecting evaporated particles, 38 a collecting vessel for collecting superparamagnetic ultramicro-particles, 39 a vacuum pump, 40 a dispersion solution, 41 a magnetic filter, 42 Argon gas, 43 a leak valve, 44 a liquid nitrogen container, 45 liquid nitrogen, and 46 and 47 valves.

Firstly, 50 ml of a 10% aqueous solution of dextran (produced by Pharmacia AB; weight based mean molecular weight: 7,700) 2 was charged in the recovering vessel 38, and then liquid nitrogen 45 was poured in the liquid nitrogen container 44 to freeze the dextran solution. After evacuating the inside the atmosphere vessel 31 down to $2 \times 10^{-7}$ Torr using a turbo-molecular pump 36, the valve 46 was closed, and the leak valve 43 was opened to introduce argon gas 42. Next, the valve 47 was opened and argon gas was evacuated with the oil-sealed rotary pump 39. By controlling the leak valve 43, the pressure of the atmosphere vessel 31 was kept to $5 \times 10^{-1}$ Torr. As the result, argon gas 42 was constantly introduced into the recovering vessel 38 from the atmosphere vessel 31 through the collecting tube 37, and then evacuated to the outside by the oil-sealed rotary pump 39.

Then, the magnetic filter 41 made of an electromagnet was actuated with applying magnetic field of 1,000 Gauss inside the collecting tube in the direction at right angles to the collecting tube 37. After these operations, laser beam 34 from YAG laser 33 of 10 watts was guided to the atmosphere vessel 31 by means of the mirror 35, to heat and evaporate the starting material 32 to be evaporated made of iron of purity of 99.9%, thus forming micro-particles of iron. The iron micro-particles together with argon gas were conveyed to the recovering vessel 38 through the magnetic filter 41, during which operation ferromagnetic micro-particles were collected by the magnetic filter 41 and only superparamagnetic ultramicro-particles reached the recovering vessel 38. Since the dextran solution in the recovery vessel was frozen, the superparamagnetic ultramicro-particles deposited on the surface of the frozen dextran solution. After a predetermined amount of iron was evaporated, the liquid nitrogen container 44 was lowered by a known means (not shown) so that the recovery vessel went out of the liquid nitrogen to elevate the temperature thereof back to room temperature. The superparamagnetic ultramicro-particles of iron deposited on the frozen surface of the dextran solution came to be dispersed in the resulting dextran solution according as the frozen solid melted, during which dextran was absorbed on the surface of the ultramicro-particles of iron to give superparamagnetic ultramicro-particles of a mean particle size of 10 nm.

Then, controlling the operational conditions including laser output, the pressure of argon gas, the magnetic field of the magnetic filter 41, similarly to the above, superparamagnetic ultramicro-particles of a mean particle size in the range of 5 to 20 nm were obtained, and IgG antigens to type A or B influenza virus was immobilized to the particles by forming covalent bonding therebetween in the same manner as in Example 5 above to obtain superparamagnetic-labeled bodies.

Using the interference method described above and a direct method in which $1 \times 10^{-8}$ g of the above-described superparamagnetic-labeled bodies were each added to 1 ml of a specimen collected from gargled water from a patient detection was performed, and as the result both type A and type B viruses were identified with a detection sensitivity by about 100,000 times as high as the conventional blood cell agglutination method.

EXAMPLE 7

Figures 10A, 10B, 10C:
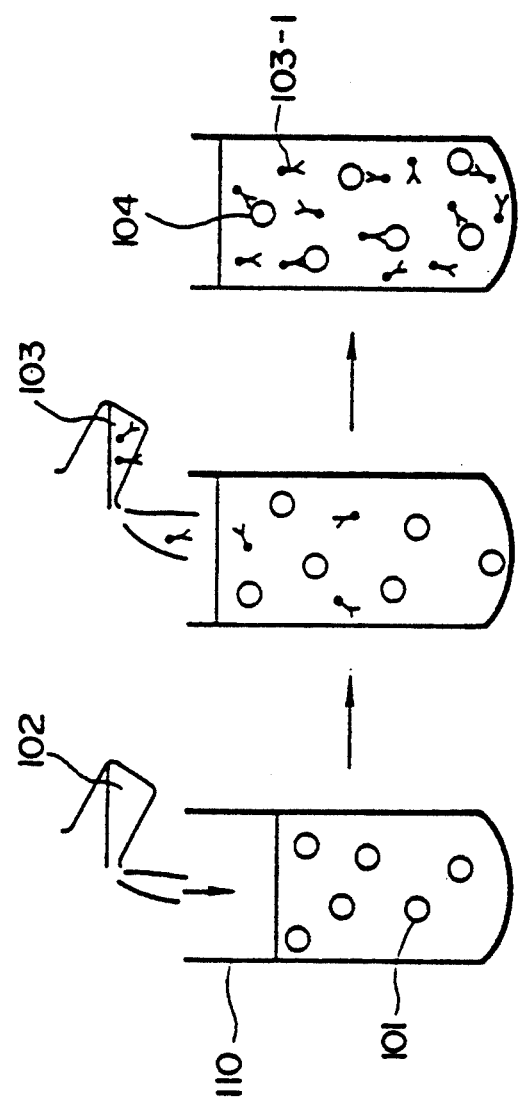
FIGS. 10a, 10b, 10c are schematic diagrams illustrating a step of preparing a specimen in which FIG. 10(a) indicates a step of introducing a buffer solution, FIG. 10(b) a step of pouring a superparamagnetic-labeled body, and FIG. 10(c) a step of incubating.

FIG. 10(a)–(c) illustrate schematically an example of the method for the preparation of specimen according to the sixth embodiment of the present invention, in which FIG. 10(a) is a step of pouring a buffer, FIG. 10(b) a step of pouring magnetic-labeled body, and FIG. 10(c) is a step of incubating. This example was performed to confirm the principle on which the laser magnetic immunoassay method according to the sixth embodiment of the present invention using inactivated influenza virus which is highly safe when performing experiments.

In FIG. 10, reference numeral 101 indicates influenza virus, 102 a PBS buffer, 103 a magnetic-labeled body, 103-1 an unreacted magnetic-labeled body, 104 a magnetic-labeled immunocomplex, and 110 a specimen container.

The PBS buffer solution 102 was added to influenza virus (A/Ishikawa (H3N2) 101 inactivated with formalin (30% aqueous formaldehyde solution) and purified by ultracentrifugation to make 20 ml of a virus suspension, to which was added 25 μm of the magnetic-labeled body 103 which was obtained by combining the dextran-coated magnetic micro-particles composed of magnetite with IgG antibody isolated from rabbit hyperimmune antiserum to influenza by covalent bond. The mixture was incubated at 35° C. for 2 hours to magnetically label the virus. In the specimen container 110 after the cultivation step were coexisting magnetic-labeled immunocomplex 104 and unreacted magnetic-labeled body 103-1. The dextran-coated magnetic particles were prepared by the method described in U.S. Pat. No. 4,452,773 to Robert S. Molday, "Magnetic Iron-Dextran Microspheres".

Figure 11:
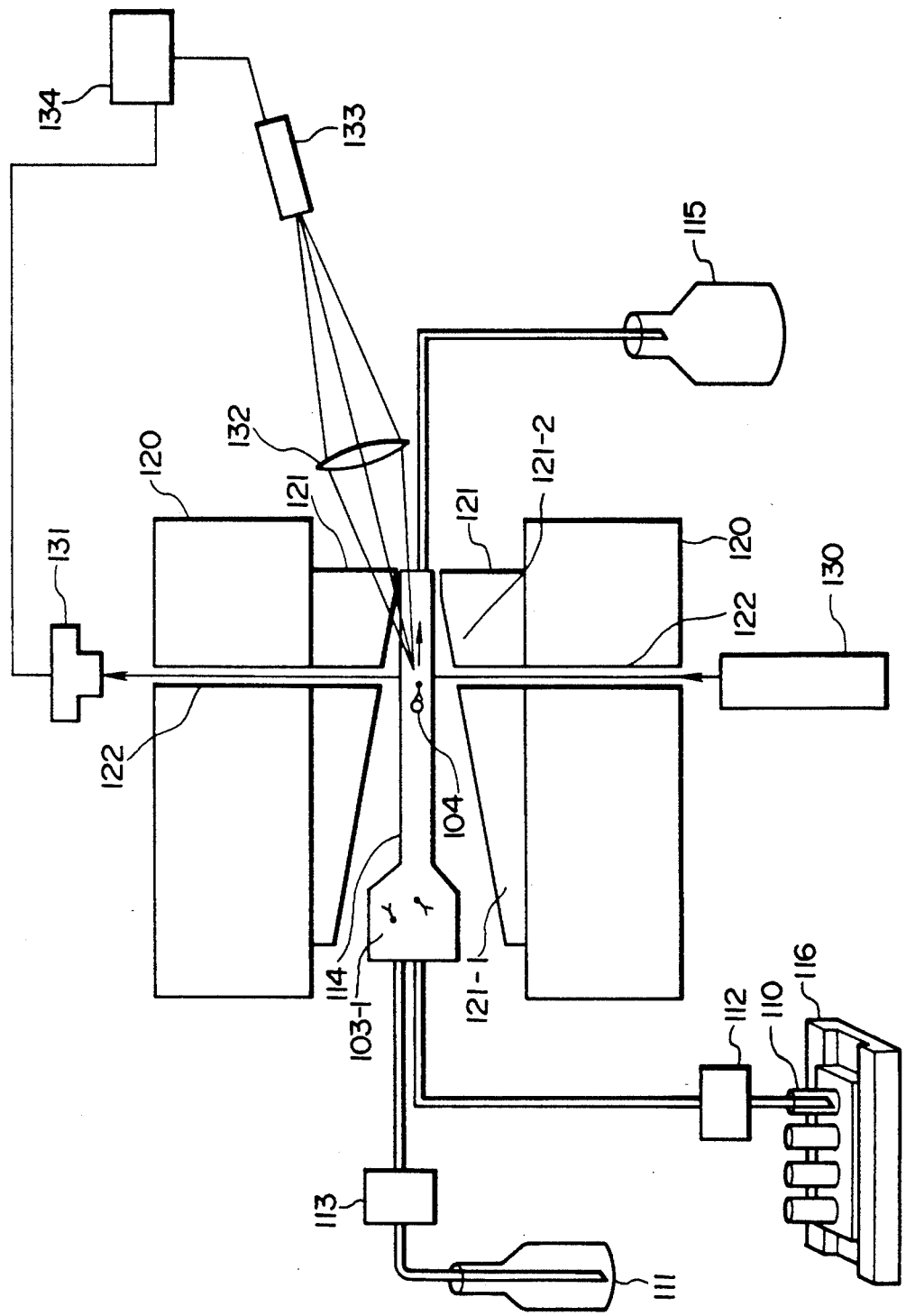
FIG. 11 is a schematic side view of an apparatus according to an embodiment of the present invention.

FIG. 11 is a schematic side view of a laser magnetic immunoassay apparatus according to the seventh embodiment of the present invention, in which reference numeral 111 is a container for holding a solvent serving also as a washing liquor, 112 a micro-pump for transporting a specimen, 113 a micro-pump for transporting the solvent/washing liquor, 114 a magnetophoretic tube, 115 a container for holding waste liquor, 116 a sample autochanger, 120 an electromagnet, 121 a magnetic pole for generating gradient magnetic field, 121-1 a lower magnetic field side of the magnetic pole, 121-2 a higher magnetic field side of the magnetic pole, 122 a through hole formed in the electromagnet and the gradient magnetic field generating poles, 130 a laser beam source, 131 a detector for transmitted light, 132 a condenser lens for condensing scattered light, 133 a photomultiplier, and 134 an electronic circuit.

The magnetophoretic tube 114 made of transparent glass was inserted fixedly held between the electromagnet 120 and the pole 121 by a supporting means (not shown). Since pole 121 had a tapered shape, the magnetic gap length was the smaller the more approaching the right hand side end of the pole 121 in FIG. 11. That is, the right hand side portion 122-2 of the pole 121 was higher magnetic field side in magnetic field, and the left hand side portion 122-1 of the pole was lower magnetic side. In the apparatus used in this example, the lower magnetic field side 121-1 was set at 7 kG and the higher magnetic field side 122-2 at 12 kG, and the total length of the magnetophoretic tube 114 was 40 mm. The magnetic substances placed inside the magnetophoretic tube 114 were attracted by magnetic force from the lower magnetic field side to the higher magnetic field side, and therefore they were transported from the left hand side to the right hand side in the magnetophoretic tube 114 along the length thereof. On the end surface at the lower magnetic field side 121-1 of the magnetophoretic tube 114 was attached a tube for introducing the specimen and the solvent/washing liquor. The specimen and the solvent/washing liquor were poured into the magnetophoretic tube through the micro-pumps 112 and 113, respectively. On the end surface of the higher magnetic field side of the magnetophoretic tube 114 was attached a tube for discharging the specimen on which measurement was completed. The other end of the tube 114 was introduced to the container 115 for holding or storing waste liquor.

The laser beam put out from the He-Ne laser beam source 130 at a wavelength of 632.8 nm and output power of 5 mW traveled through a through hole 122 with a diameter of 1.5 mm and entered as an incident beam to the magnetophoretic tube 114, and transmitted light therefrom entered the detector 131 made of Si for detecting transmitted light photodiode, passing through the through hole 122 again. The output from the detector 131 was analyzed for the time response characteristics of transmitted light by the electronic circuit 134. On the other hand, scattered light from the magnetic-labeled immunocomplex 104 and that of unreacted magnetic-labeled body 103-1 in the magnetophoretic tube 114 were guided to the photomultiplier 133 through the condensing lens 132 for condensing the scattered lights, and output from the photomultiplier 133 was analyzed by the electronic circuit 134 to obtain time response characteristic of the scattered lights.

Next, the operational procedures in which the apparatus was used are described. The specimen container 110 after preparation of the specimen as shown in FIG. 10 was set in the sample autochanger 116. A first specimen was poured in the magnetophoretic tube 114 by actuating the micro-pump 112 for transporting the first specimen after pouring the solvent/washing liquor in the magnetophoretic tube 114 and filling it with the solvent. Then, the electromagnet 120 was energized, and time response of scattered light or transmitted light starting from the time when the magnetophoresis was begun was recorded and analyzed. After completion of measurement, the energization of the electromagnet 120 was stopped followed by actuating the micro-pump 113 to remove the specimen in the tube 114 and washing the inside the tube 114. Thereafter, the sample autochanger 116 was actuated to pour a second specimen into the magnetophoretic tube 114. Thus, a plurality of specimens were successfully measured automatically.

Figure 12:
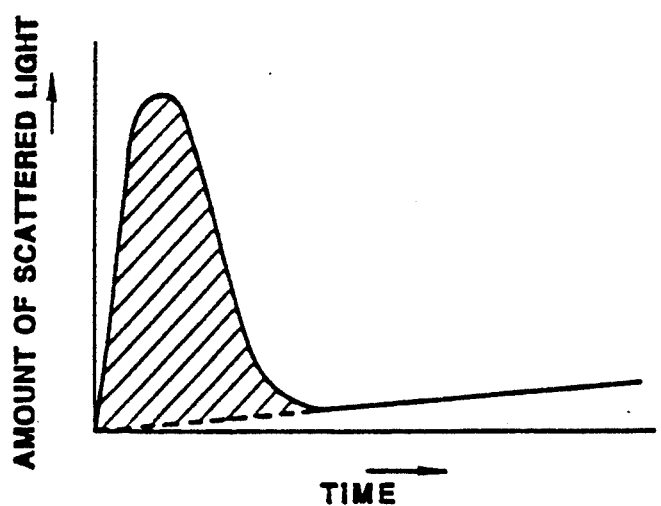
FIG. 12 is graph plotting data on a specimen in which virus is present.
Figure 13:
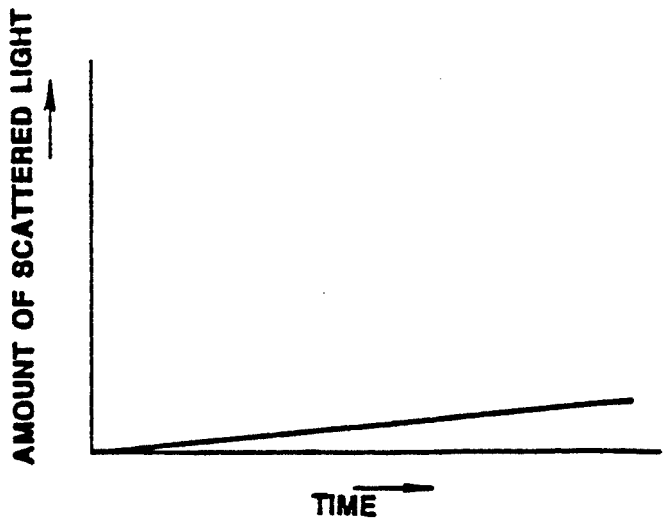
FIG. 13 is a graph plotting data on a control specimen which was treated in the same manner as the specimen but did not harbor any virus to be checked.

FIG. 12 shows data from the specimen in which virus was present, and FIG. 13 shows data on specimen control obtained by performing the same treatments as the specimen but containing no virus, both showing change in the amount of scattered light with lapse of time. When the specimen or virus was present, the amount of scattered light therefrom increased immediately after the energization of the electromagnet 120 and decreased again. The change in the amount of scattered light was proportional to the amount of the magnetic-labeled immunocomplex 104 which passed the position of laser beam radiation by magnetophoresis. On the contrary, the amount of scattered light from the specimen control increased only a little with lapse of time. Thus, determination of only the specimen was successful by detecting the chronological change in the amount of scattered light from the specimen and deducing the amount of the specimen control therefrom. Measurement of the specimen control may be performed as the occasion demands. For example, it is preferred to measure the specimen control only once before a series of specimens are measured, and record data on a memory device.

Using the immunoassay method according to the sixth embodiment of the present invention, influenza virus, whose detection needed cultivation when measured by the conventional methods, was able to detect directly by performing simple preparation of specimens. In this example, influenza virus in a population in the order of 100 individuals/ml were successfully measured.

Although this example use a method in which laser beam was radiated at a position in a magnetophoretic tube where a specimen passed and scattered light or transmitted light was detected, a variation may be used in which laser beam is radiated to the position of concentration where the concentration of a specimen is highest. In the latter, however, scattering volume will increase and light scattering mechanism will be switched from Rayleigh scattering to Mie scattering when the concentration of a specimen is high and there may be sometimes a problem in the accuracy in quantitative determination.

EXAMPLE 8

In order to examine applicability of the laser magnetic immunoassay of the present invention, detection of B cell lymphocytes infected with EB virus, which is highly safe to humans when performing experiments, was carried out as a model experiment for the detection of cells. As for the EB virus-infected lymphocyte was used Burkitt lymphoma-derived cells, ATCC CCL-86 RAJI cell, and non-infections lymphocyte Bri7 derived from healthy subject was used for comparison. The lymphocyte cells were cultivated.

What is claimed is:

1. A laser magnetic immunoassay method comprising:
   (a) subjecting a superparamagnetic-labeled free antigen or antibody comprising an antigen or an antibody attached to a superparamagnetic microparticle, to an immunoreaction with a specimen containing a target antibody or a target antigen to form an analyte solution containing superparamagnetic-labeled immunocomplexes;
   (b) applying a magnetic field gradient generated by an electromagnet and a magnetic pole piece arranged opposite the electromagnet so as to preferentially concentrate said immunocomplexes to a predetermined position of concentration;
   (c) radiating a laser beam on said predetermined position of concentration;
   (d) detecting and measuring the intensity of scattered or reflected outgoing light;
   (e) distinguishing between said superparamagnetic-labeled free antigen or antibody and said superparamagnetic-labeled immunocomplexes by a change in the scattered or reflected outgoing light caused by a difference in time in which said superparamagnetic-labeled free antigen or antibody and said superparamagnetic-labeled immunocomplexes reach the position of concentration.

2. The laser magnetic immunoassay method as claimed in claim 1, wherein the immunoreaction in the step (a) is performed in a magnetic field to effect alignment of the direction of magnetization of the superparamagnetic-labeled immunocomplexes obtained after the immunoreaction.

3. The laser magnetic immunoassay method as claimed in claim 1, wherein the specimen comprises virus cells, cancer cells or lymphocytes.

4. The laser magnetic immunoassay method as claimed in claim 3, wherein the specimen comprises a virus and the virus is an influenza virus.

5. The laser magnetic immunoassay method as claimed in claim 1, wherein the superparamagnetic microparticle is not larger than 10 nm when the ferromagnetic substance is magnetite or gamma-ferrite and is not larger than 3 nm when the ferromagnetic substance is pure iron.

* * * * *